US005378620A

United States Patent [19]

Adams et al.

[11] Patent Number: 5,378,620

[45] Date of Patent: Jan. 3, 1995

[54] STREPTOLYSIN O DERIVATIVES

[75] Inventors: Craig W. Adams, Corona; Eva Y. Wang, Tustin, both of Calif.

[73] Assignee: Beckman Instruments, Inc., Fullerton, Calif.

[21] Appl. No.: 752,429

[22] Filed: Aug. 30, 1991

[51] Int. Cl.[6] .......................... C12N 9/00; C12N 1/20; C12P 21/06; C07H 19/00

[52] U.S. Cl. .................................... 435/183; 435/69.1; 435/252.3; 435/320.1; 536/22.1; 536/23.1; 536/23.2; 536/23.7

[58] Field of Search ..................... 435/183, 69.1, 252.3, 435/320.1; 536/22.1, 23.1, 23.2, 23.7

[56] References Cited

U.S. PATENT DOCUMENTS 4,925,799 5/1990 Rosenberg .

FOREIGN PATENT DOCUMENTS 2003307 5/1990 Canada .

OTHER PUBLICATIONS

Kehoe et al. "Cloning and Expression in *Escherichia coli* of the Streptolysin O Determinant from *Streptococcus pyogenes*"; *Infect Imm.* 43:804–810 (1984).

Kehoe, M. A. et al. "Nucleotide Sequence of the Streptolysin O (SLO) Gene: Structural Homologies between SLO and Other Membrane-Damaging, Thiol-Activated Toxins"; *Infect. Imm.* 55:3228–3232 (1987).

Becker, J. et al. "Nephelometric Determination of Anti-streptolysin O." AACC 1991 Meeting, Washington, D.C. (Aug. 1, 1991).

Shatzman, A. R. & Rosenberg, M. "Expression Identification, and Characterization of Recombinant Gene Products in *Escherichia coli.*" *Methods in Enzymology* 152:661–675 (1987).

Shatzman, A. R. & Rosenberg, M. "The pAS Vector System and Its Application to Heterologous Gene Expression in *Escherichia coli.*" *Hepatology* 7:305–355 (1987).

Degnen, G. A. & Cox, E. C. "Conditional Mutator Gene in *Escherichia coli:* Isolation, Mapping and Effector Studies." *J. Bacter.* 117:477–487 (1987).

Echols, H. et al. "Mutator Strains of *Escherichia coli,* mutD and DnaQ, with defective exonucleolytic editing by DNA polymerase III holoenzyme." *PNAS USA* 80:2189–2192 (1983).

Schaaper, R. M. "Mechanisms of mutagenesis in the *Escherichia coli* mutator mutD5: Role of DNA mismatch repair." *PNAS USA* 85:8126–8130 (1986).

Alouf, J. E. "Streptococcal Toxins (Streptolysin O, Streptolysin S, Erythrogenic Toxin)." *Pharmac. Ther.* 11:661–717 (1980).

*Primary Examiner*—Robert A. Wax
*Assistant Examiner*—Hyosuk Kim
*Attorney, Agent, or Firm*—William H. May; P. R. Harder; Janis C. Henry

[57] ABSTRACT

Disclosed herein are derivatives of Streptolysin 0 produced by recombinant DNA techniques. In an embodiment, the derivative is soluble upon expression and has a specific hemolytic activity of about $3.6\times10^4$ hemolytic units per milligram.

6 Claims, 4 Drawing Sheets

ATG GAT CCG TCA GAA GAC AAA AAA AAG AGC GAA GAA GAT CAC ACT GAA 48

GAA ATC AAT GAC AAG ATT TAT TCA CTA AAT TAT AAT GAG CTT GAA GTA 96

CTT GCT AAA AAT GGT GAA ACC ATT GAA AAT TTT GTT CCT AAA GAA GGC 144

GTT AAG AAA GCT GAT AAA TTT ATT GTC ATT GAA AGA AAG AAA AAA AAT 192

ATC AAC ACT ACA CCA GTC GAT ATT TCC ATC ATT GAC TCT GTC ACT GAT 240

AGG ACC TAT CCA GCA GCC CTT CAG CTG GCT AAT AAA GGT TTT ACC GAA 288

AAC AAA CCA GAC GCG GTA GTC ACC AAG CGA AAC CCA CAA AAA ATC CAT 336

ATT GAT TTA CCA GGT ATG GGA GAC AAA GCA ACG GTT GAG GTC AAT GAC 384

CCT ACC TAT GCC AAT GTT TCA ACA GCT ATT GAT AAT CTT GTT AAC CAA 432

TGG CAT GAT AAT TAT TCT GGT GGT AAT ACG CTT CCT GCC AGA ACA CAA 480

TAT ACT GAA TCA ATG GTA TAT TCT AAG TCA CAG ATT GAA GCA GCT CTA 528

AAT GTT AAT AGC AAA ATC TTA GAT GGT ACT TTA GGC ATT GAT TTC AAG 576

TCG ATT TCA AAA GGT GAA AAG AAG GTG ATG ATT GCA GCA TAC AAG CAA 624

ATT TTT TAC ACC GTA TCA GCA AAC CTT CCT AAT AAT CCT GCG GAT GTG 672

TTT GAT AAA TCA GTG ACC TTT AAA GAG TTG CAA CGA AAA GGT GTC AGC 720

AAT GAA GCT CCG CCA CTC TTT GTG AGT AAC GTA GCC TAT GGT CGA ACT 768

GTT TTT GTC AAA CTA GAA ACA AGT TCT AAA AGT AAT GAT GTT GAA GCG 816

GCC TTT AGT GCA GCT CTA AAA GGA ACA GAT GTT AAA ACT AAT GGA AAA 864

TAC TCT GAT ATC TTA GAA AAT AGC TCA TTT ACA GCT GTC GTT TTA GGA 912

GGA GAT GCT GCA GAG CAC AAT AAG GTA GTC ACA AAA GAC TTT GAT GTT 960

ATT AGA AAC GTT ATC AAA GAC AAT GCT ACC TTC AGT AGA AAA AAC CCA 1008

FIG. 1

```
GCT TAT CCT ATT TCA TAC ACC AGT GTT TTC CTT AAA AAT AAT AAA ATT   1056

GCG GGT GTC AAT AAC AGA ACT GAA TAC GTT GAA ACA ACA TCT ACC GAG   1104

TAC ACT AGT GGA AAA ATT AAC CTG TCT CAT CAA GGC GCG TAT GTT GCT   1152

CAA TAT GAA ATC CTT TGG GAT GAA ATC AAT TAT GAT GAC AAA GGA AAA   1200

GAA GTG ATT ACA AAA CGA CGT TGG GAT AAC AAC TGG TAT AGT AAG ACA   1248

TCA CCA TTT AGC ACA GTT ATC CCA CTA GGA GCT AAT TCA CGA AAT ATA   1296

CGT ATC ATG GCT AGA GAG TGC ACC GGC TTA GCT TGG GAA TGG TGG CGA   1344

AAA GTG ATC GAC GAA AGA GAT GTG AAA CTG TCT AAA GAA ATC AAT GTC   1392

AAC ATC TCA GGA TCA ACC CTG AGC CCA TAT GGT TCG ATT ACT TAT AAG   1440

TAG GAC TGG TTC AAG AGG TTC GTC AAG CAC CTT GAT GCT GCT TAT CTC   1488

TTG AGA TCC CCG GGT AGG CCT AGT TAA CTA GTC GAC                   1524
```

FIG. 1
(Continued)

```
Met Asp Pro Ser Glu Asp Lys Lys Lys Ser Glu Glu Asp His Thr Glu
 -2  -1                  5                  10

Glu Ile Asn Asp Lys Ile Tyr Ser Leu Asn Tyr Asn Glu Leu Glu Val
15                  20                  25                  30

Leu Ala Lys Asn Gly Glu Thr Ile Glu Asn Phe Val Pro Lys Glu Gly
                35                  40                  45

Val Lys Lys Ala Asp Lys Phe Ile Val Ile Glu Arg Lys Lys Lys Asn
            50                  55                  60

Ile Asn Thr Thr Pro Val Asp Ile Ser Ile Ile Asp Ser Val Thr Asp
        65                  70                  75

Arg Thr Tyr Pro Ala Ala Leu Gln Leu Ala Asn Lys Gly Phe Thr Glu
    80                  85                  90

Asn Lys Pro Asp Ala Val Val Thr Lys Arg Asn Pro Gln Lys Ile His
95                  100                 105                 110

Ile Asp Leu Pro Gly Met Gly Asp Lys Ala Thr Val Glu Val Asn Asp
                115                 120                 125

Pro Thr Tyr Ala Asn Val Ser Thr Ala Ile Asp Asn Leu Val Asn Gln
            130                 135                 140

Trp His Asp Asn Tyr Ser Gly Gly Asn Thr Leu Pro Ala Arg Thr Gln
        145                 150                 155

Tyr Thr Glu Ser Met Val Tyr Ser Lys Ser Gln Ile Glu Ala Ala Leu
    160                 165                 170

Asn Val Asn Ser Lys Ile Leu Asp Gly Thr Leu Gly Ile Asp Phe Lys
175                 180                 185                 190

Ser Ile Ser Lys Gly Glu Lys Lys Val Met Ile Ala Ala Tyr Lys Gln
                195                 200                 205

Ile Phe Tyr Thr Val Ser Ala Asn Leu Pro Asn Asn Pro Ala Asp Val
            210                 215                 220

Phe Asp Lys Ser Val Thr Phe Lys Glu Leu Gln Arg Lys Gly Val Ser
        225                 230                 235
```

FIG. 2

```
 Asn Glu Ala Pro Pro Leu Phe Val Ser Asn Val Ala Tyr Gly Arg Thr
     240                 245                 250

 Val Phe Val Lys Leu Glu Thr Ser Ser Lys Ser Asn Asp Val Glu Ala
255                 260                 265                 270

 Ala Phe Ser Ala Ala Leu Lys Gly Thr Asp Val Lys Thr Asn Gly Lys
                 275                 280                 285

Tyr Ser Asp Ile Leu Glu Asn Ser Ser Phe Thr Ala Val Val Leu Gly
             290                 295                 300

 Gly Asp Ala Ala Glu His Asn Lys Val Val Thr Lys Asp Phe Asp Val
         305                 310                 315

 Ile Arg Asn Val Ile Lys Asp Asn Ala Thr Phe Ser Arg Lys Asn Pro
     320                 325                 330

 Ala Tyr Pro Ile Ser Tyr Thr Ser Val Phe Leu Lys Asn Asn Lys Ile
335                 340                 345                 350

 Ala Gly Val Asn Asn Arg Thr Glu Tyr Val Glu Thr Thr Ser Thr Glu
                 355                 360                 365

 Tyr Thr Ser Gly Lys Ile Asn Leu Ser His Gln Gly Ala Tyr Val Ala
             370                 375                 380

 Gln Tyr Glu Ile Leu Trp Asp Glu Ile Asn Tyr Asp Asp Lys Gly Lys
         385                 390                 395

 Glu Val Ile Thr Lys Arg Arg Trp Asp Asn Asn Trp Tyr Ser Lys Thr
     400                 405                 410

 Ser Pro Phe Ser Thr Val Ile Pro Leu Gly Ala Asn Ser Arg Asn Ile
415                 420                 425                 430

 Arg Ile Met Ala Arg Glu Cys Thr Gly Leu Ala Trp Glu Trp Trp Arg
                 435                 440                 445

 Lys Val Ile Asp Glu Arg Asp Val Lys Leu Ser Lys Glu Ile Asn Val
             450                 455                 460

 Asn Ile Ser Gly Ser Thr Leu Ser Pro Tyr Gly Ser Ile Thr Tyr Lys
         465                 470                 475
```

FIG. 2
(continued)

STREPTOLYSIN O DERIVATIVES

37 C.F.R. §1.74 (D) /(E) COPYRIGHT NOTICE

A portion of the disclosure of this patent document contains material which is subject to copyright protection. The copyright owner does not object to the reproduction by anyone of the patent document or the patent disclosure, as it appears in the Patent and Trademark Office patent file or records, but otherwise reserves all copyright rights whatsoever.

RELATED APPLICATIONS

This application is related to U.S. Ser. No. 07/752,428, filed Aug.30, 1991 entitled "Streptolysin O Variants" by Craig W. Adams, and U.S. Ser. No. 07/753,289, filed Aug. 30, 1991, entitled "Antibodies to Streptolysin O Derivatives and Varients", by Craig W. Adams and Patty Pang. Both applications are being filed simultaneously herewith, and both are incorporated herein by reference.

Field of the Invention

The present invention is generally related to Streptolysin O and more particularly to Streptolysin O derivatives produced by recombinant DNA technology.

Background of the Invention

Disclosed herein is a derivative fusion product of the antigenic substance, Streptolysin O Streptolysin O is associated in humans with, for example, rheumatic fever, such that immunodiagnostic assays for evidence of immunological response against Streptolysin O are routinely utilized. The disclosed derivative version of Streptolysin is produced by recombinant DNA techniques, is soluble upon expression, is capable of being bound by at least one antibody capable of binding to wild type SLO, and is hemolytically active. Prior to this invention, Streptolysin O could be obtained via the bacterial *Streptococcus pyogenes*. The toxic and pathogenic properties of Streptolysin O are typically monitored by the lysis of red blood cells.

I. The Genetic Code

The genetic code for a particular protein, such as Streptolysin O (hereinafter "SLO"), depends upon the sequential grouping of three nucleotides, referred to as a "codon," and the arrangement of such codons in relationship to each other.

A "nucleotide" consists of a nucleoside and one or more phosphate groups. A "nucleoside" consists of a nitrogeneous base linked to a pentose sugar. A "pentose" sugar comprises five carbon atoms. In a molecule of deoxyribonucleic acid, or "DNA", the pentose sugar is "deoxyribose," and the nitrogeneous base can be adenine ("A"), guanine ("G"), thymine ("T") or cytosine ("C"). In a molecule of ribonucleic acid, or "RNA", the pentose sugar is "ribose", and the nitrogeneous bases are the same for DNA, except uracil ("U") replaces thymine Three types of RNA, messenger RNA, or "mRNA", transfer RNA, or "tRNA", and ribosomal, or "rRNA", translate the genetic information encoded in the DNA into, e.g., a polypeptide or a protein. Thus, genetic information is generally transferred as follows: DNA→RNA→protein.

The sequence of the nitrogenous bases of the DNA molecule encodes the genetic information contained in that molecule. The sugar and phosphate groups of the DNA molecule perform a structural role, forming the backbone of a series of DNA molecules, referred to as a DNA "macromolecule." DNA consists of two complementary strands of nucleotide chains, and these strands are held together by (relatively) weak hydrogen bonds. The bases of each DNA molecule bind to each other: A always bonds with T and C always bonds with G. Thus, the sequence 5'-ATCG-3' of a first strand lies immediately opposite a complementary sequence 5'-TAGC-3' on the other strand. This is referred to as "complementary base pairing." The process of complementary base pairing is referred to as "hybridization" and results in the formation of a stable DNA macromolecule.

Each codon specifies one amino acid. "Amino acids" are the principal components of proteins, and "proteins" are the essential constituents of all living cells. There are 20 natural amino acids. Because there are four nucleotide bases (A, C, G and T) and three nucleotides per codon, there are 64 possible codons ($4^3$). Accordingly, because there are only 20 natural amino acids, most amino acids are specified by more than one codon. This is referred to as "redundancy" or "degeneracy". For example, the codons GCG, GCA, GCT and GCC all encode for the amino acid Alanine.

The codon ATG (Met amino acid codon) is the normal "start" codon. The codons TAA, TAG and TGA, which do not encode for amino acids, are the normal "stop" codons. The formation of mRNA is established based upon the start codon of one strand of the double stranded DNA macromolecule such that the resulting single stranded mRNA will have a nucleotide sequence complementary to the sequence of a single strand of the DNA. When a stop codon is reached by the mRNA along the DNA molecule, translation is stopped.

The regions along the DNA macromolecule which are translated from the mRNA are referred to as "exons" for eukaryotes, and "translated regions" for prokaryotes. "Genes" include exons (eukaryotes) and translated regions (prokaryotes). Thus, genes encode for proteins and/or polypeptides. Mammals, for example, are eukaryotes; bacteria, for example, are prokaryotes.

The natural synthesis of protein takes place over a series of several steps. The first step is the formation of an mRNA macromolecule complementary to the DNA macromolecule, as noted above. Thereafter, tRNA is manufactured; the tRNA provides a complementary codon ("anti-codon") for each codon on the mRNA macromolecule. Thereafter, rRNA will catalyze the assembly of the codon-specific amino acids resulting from the mRNA:tRNA into proteins and/or polypeptides.

II. Recombinant DNA Technology

Most proteins are produced naturally in extremely small quantities. The advent of recombinant DNA technology has allowed for the production of large quantities of proteins that were previously only available in such small quantities.

The following describes a "typical" genetic manipulation as it might apply to *Escherichia coli*, a typical bacterial host used for cloning.

In order to isolate, or "clone" a gene a DNA library is constructed from a DNA sequence (referred to as a "genome") using vectors. A "vector" is a small circular molecule of double-stranded DNA that occurs naturally in bacteria, yeast and mammalian cells. Vectors generally comprise the following characteristics: (i) a DNA sequence encoding a selectable "marker" which assures that the vector will be maintained in an appropriate host cell (e.g., *E. coli*); (ii) a controllable transcriptional promoter—by "controllable" is meant that the promoter can be "switched on" by manipulation of, e.g. the environment of the vector; a "promoter" is a region of DNA sequence that when switched on produces large amounts of mRNA from the gone of interest inserted into the vector-different promoters (e.g., lac, trp, tac, etc.) have different rates of mRNA production; (iii) translational control sequences, for example, an appropriately positioned ATG start codon; and (iv) a polylinker; a "polylinker" simplifies the insertion of the gene of interest in the correct orientation within the vector. Vectors can be engineered to provide restriction endonuclease sites on either side of an ATG start codon located on the vector such that the gene of interest can be inserted next to the start codon; this allows for immediate transcription of the gene upon activation of the promoter gene.

A "restriction endonuclease" is an enzyme which cuts the double-stranded DNA at specified sequences of four to eight nucleotides in length, and many restriction endonucleases produce staggered cuts that leave a short, single-stranded tail at the location. of the cut. This end is referred to as a "cohesive" or "sticky" end because it can form complementary base pairs with another sticky end. The genome is cleaved (cut-up) by a specified restriction endo-nuclease corresponding to the restriction endo-nuclease used to cut the vector, and the individual pieces of the cleaved genome are inserted into the vector. Randomly cleaving the entire genome of a cell with a specific restriction endo-nuclease is typically referred to as the "shotgun" approach to gene cloning. The shotgun approach can produce an extremely large number of DNA fragments, all of which are inserted into vectors.

The individual pieces of the genome and the vectors, having corresponding sticky ends, are "fused" or "annealed" together to form circular hybrid DNA "plasmids" comprising a portion of the genome and the vector.

The plasmids are then introduced into host cells. There are two types of host cells, "eukaryotic" and "prokaryotic". An example of a eukaryotic host cell is the chinese hamster ovary ("CHO"); an example of a prokaryotic host cell is *E. coli* bacteria. For purposes of the discussion to follow, attention will focus on prokaryotic host cells.

When the plasmids are introduced into the host cell, these cells are referred to as being "transformed" with the plasmids. As the cells grow and divide, the plasmids will similarly replicate to produce copies of the plasmids containing the DNA fragments. Each transformed cell is referred to as a "genomic DNA clone" and the entire collection of transformed cells containing all of the different DNA fragments is referred to as a "genomic DNA library".

In order to determine which genomic DNA clones contain the DNA sequence capable of being copied into a corresponding mRNA, it is necessary to separate or "screen" the genomic DNA clones. There are several ways to accomplish this task including, for example, the use of radioactive DNA probes or evidence of immunoreactivity. Screening can be an extremely labor intensive process because, as noted, the shotgun approach by definition leads to the formation of an extensive number of genomic DNA clones, which must be screened to find potential candidates of interest. III. Streptolysin O Streptolysin O ("SLO") has an approximate molecular weight of between about 65,000 and about 70,000 daltons. SLO belongs to a class of oxygen sensitive ("thiol-activated"), cell destroying ("cytolytic") toxin ("cytotoxin") which are produced by gram-positive bacterial species belonging to four different genera (Streptococcus, Bacillus, Clostridium and Listeria).

SLO interacts with membrane cholesterol and exerts cytolytic-cytotoxic effects on a broad range of mammalian cells. Additionally, SLO has very potent cardiotoxic properties. One of the toxic and pathogenic properties associated with SLO is its hemolytic activity, i.e. SLO will lyse red blood cells, resulting in the release of hemoglobin. SLO can be lethal to laboratory animals in relatively small doses. Injection of SLO into an animal typically results in its immediate death.

Because SLO is produced by specified bacterial species, when these species "invade" a mammalian host, the SLO released by the bacteria is treated by the host as a foreign protein. SLO, then, is an antigen. "Antigens" are high molecular weight compounds which upon entry into the blood stream of a vertebrate stimulate the transformation of the small lymphocytes of the B-type into lymphoblasts. The lymphoblasts secrete antibodies specific to the antigen stimulator. The antibodies are proteins possessing reactive sites specifically complementary to a reactive feature or site on the stimulating antigen. Antibodies generally have the property of rendering the antigen harmless to the host organism by occupying the immunologically active sites, or "epitopes", on the antigen particles or molecules. Anti-SLO antibodies ("ASO") are therefore produced by the host in response to the secretion of SLO into the host. Approximately 80–85% of individuals with current streptococcal infection or their sequelae (an after effect of a disease or injury) will demonstrate elevated levels of ASO.

Determination of previous and/or current infection by the specified bacterial species which secretes SLO is possible using immunodiagnostic assaying techniques which, e.g., rely upon the hemolytic properties of SLO and the binding of ASO to SLO. Focusing on hemolytic immunodiagnostic assays for SLO, a patient sample is added to a known amount of SLO derived from a source other than the patient and this mixture is added to a known amount of red blood cells such as, for example, rabbit red blood cells. Because SLO has hemolytic properties, it will lyse these red blood cells. However, when ASO binds to SLO, the hemolytic properties of SLO are neutralized. Thus, if the sample is obtained from a patient having current streptococcal infection or their sequelae, there will be elevated levels of ASO in the sample. Accordingly, if the mixture results in high levels of hemolytic activity, this indicates that there is little, if any, ASO in the serum sample (and hence little, if any, infection from the SLO secreting bacteria) because the known quantity of SLO in the mixture is capable of lysing the known quantity of red blood cells in the mixture. If the mixture does not lead to hemolytic activity, this is indicative of an amount of ASO in the sample sufficient to inactivate the known quantity of SLO in the mixture. Investigators refer to such an amount of ASO as a "titer". Typically, an ASO titer of greater than about 300 International Units/ml is indicative of infection by a bacterial source capable of secreting SLO. Other immunodiagniostic assays for determination of infection by SLO secreting bacteria include nephelometric and turbidimetric protocols.

In order to utilize the immunodiagnostic assaying technique outlined above, it is necessary to have access to sufficient SLO to be added to the mixture. One source of SLO is culture broths containing the bacteria *Streptococcus pyogenes* ("*S. pyogenes*"). However, obtaining SLO in this manner is quite difficult and costly: for every liter of the *S. pyogenes* culture broth, only about 0.5 mg of SLO can be expected; the typical media for growing *S.pyogenes* is expensive; *S. pyogenes* is a class 2 pathogen; and SLO obtained in this manner contains many other antigenic materials. Additionally, SLO obtained by this procedure tends to be unstable in liquid form. Accordingly, such SLO preparations are most typically supplied as lyophilized powder in vials. Before use, the lyophilized powder must be reconstituted in a suitable solvent. Unfortunately, such reconstituted SLO will rapidly lose its hemolytic activity and therefore it must be used within a brief period after reconstitution or discarded. This has one notable and negative consequence: it is usually impossible to test individual serum samples as soon as they are obtained. Thus, laboratories which conduct ASO assays based upon hemolytic activity typically store the individual samples until a sufficient number are collected to enable economic use of the lyophilized SLO. This can result in an inordinate delay in obtaining test results.

ASO assays which rely upon nephelometric or turbidimetric protocols need significant amounts of purified SLO. Because of the costs associated with obtaining significant quantities of purified SLO from *S. pyogenes* is expensive, the foregoing hemolytic based assay was the first ASO assay to become commercially available.

Recombinant DNA techniques for obtaining SLO fusion products offer the benefit of obtaining relatively large quantities of such products. Using such technology, it would be possible to avoid the tedious and cost-ineffective aspects of obtaining SLO from *S. pyogenes*. As used herein, the term "SLO derivative" is an SLO fusion product which is soluble, hemolytically active and which is capable of being bound by at least one antibody to wild type SLO. SLO derivatives are designated herein as "rSLO". These SLO derivatives are provided in large quantities, are substantially pure, and maintain hemolytic activity.

Such SLO derivatives would be beneficial, e.g., in immunodiagnostic assays which rely upon, e.g., the hemolytic properties of wild-type SLO.

SUMMARY OF THE INVENTION

The present invention provides SLO variants. These variants, designated herein as "mSLO", comprise the following characteristics and are broadly defined thereby: (i) recognized by wild-type anti-streptolysin antibodies (ASO), i.e. comprising at least one epitope characteristic of wild-type Streptolysin O and (ii) substantially non-hemolytic activity. As used herein, the term "recognized" means capable of binding to at least one epitopic site on mSLO; the phrase "substantially non-hemolytic activity" means a percent wild-type SLO specific activity of less than about based upon a wild-type SLO specific activity of $4\times10^5$ hemolytic units/mg wild-type SLO; and "wild-type SLO" is accorded the usual definition associated with such phrase, i.e., SLO that is naturally secreted by a capable bacterial source. "Wild-type SLO", by definition, does not include, e.g., SLO fusion products derived via recombinant DNA techniques.

A particularly useful rSLO in accordance with the present disclosure is designated herein as rSLO.3 having a specific hemolytic activity of about $3.6\times10^4$ hemolytic units ("HU") per mg.

BRIEF DESCRIPTION OF THE DRAWINGS

FIG. 1 is a single strand of the nucleic acid sequence of a most preferred embodiment of an SLO derivative, designated rSLO.3; and FIG. 2 is the amino acid sequence of rSLO.3.

DETAILED DESCRIPTION OF PREFERRED EMBODIMENTS

As used in this disclosure, Streptolysin O derivatives, or "rSLO", comprise the following characteristics and are broadly defined thereby: (i) capable of being bound by at least one antibody to wild-type SLO; (ii) soluble upon expression; and (ii) hemolytically active. As used herein, the phrase "wild-type SLO" is accorded the usual definition associated with such phrase, i.e., SLO that is naturally secreted by a bacterial source capable of secreting such protein. Preferably, the hemolytic activity of rSLO has about 75% of the hemolytic activity of wild-type SLO, based upon a wild-type SLO specific activity of $4\times10^5$ hemolytic units/mg. More preferably, the hemolytic activity of rSLO is between about 5% and 50%, and most preferably about 9%, of the hemolytic activity of wild-type SLO, based upon a wild-type SLO specific activity of $4\times10^5$ hemolytic units/mg wild-type SLO. These values are relative; thus, if percent wild-type SLO specific activity is based upon a wild-type SLO specific activity of $1\times10^6$ hemolytic units/mg, the above values are decreased by a factor of 2.5 (i.e., 75% becomes 30%; 9% becomes 3.6%; etc.

The preceding is detailed because the "specific activity" of wild-type SLO has been described as being as high as about $1\times10^6$ hemolytic units/mg, although specific activity of about $4\times10^5$ hemolytic units/mg has also been described. Alouf, J. E. "Streptococcal Toxins (Streptolysin O, Streptolysin S, Erythrogenic Toxin)." *Pharmac. Ther. II*:661–717 (1980), which is incorporated herein by reference. Accordingly, because the reported "specific activity" of wild type SLO is elusive, the foregoing percentages accomodate this fact.

For convenience, as used herein, the term "vector" means a circular DNA macromolecule comprising at least one restriction site and at least one promoter gene. The term "plasmid" means a vector further comprising a portion of a genome of interest, including, inter alia, a gene. The term "host" means a cell capable of being transfected by a plasmid.

As those in the art appreciate, most vectors are selected with respect to a desired outcome. For example, in a commercial setting, high-level expression of the gene of interest will typically be preferred such that vectors with an appropriate promoter conducive to such expression will be chosen; on the other hand, in a research setting, such high level expression may not be critical such that a vector having translational and transcriptional signals that are under the control of regulatory elements of the host may be appropriate. Accordingly, in selecting a vector appropriate for the desired outcome, it is often useful to concurrently focus on the promoter gene of the vector of interest.

Promoter genes which achieve very high levels of mRNA production include, for example, $P_L$, $P_{tac}$, and $P_{T7}$. This list is not intended, nor is it to be construed, as an exhaustive list. Rather these promoters are used as exemplars for purposes of the discussion to follow.

Those in the art can readily select an appropriate vector having a desired promoter which can provide equivalent results vis-a-vis the listed promoters.

For example, $p_{T7}$ is used in conjunction with T7 RNA polymerase which synthesizes RNA at a rate several times that of *E. coli* RNA polymerase and which terminates transcription less frequently than *E. coli* RNA polymerase. T7 RNA polymerase is highly selective for initiation at its own promoter sequence; accordingly, it does not initiate transcription from any sequences on *E. coli* DNA. Furthermore, T7 RNA polymerase is resistant to antibiotics such as rifampicin that inhibit *E. coli* RNA polymerase. Therefore, the addition of rifampicin, for example, to cells that are promoting T7 RNA polymerase results in the exclusive expression of genes under the control of a T7 RNA polymerase promoter, i.e., $p_{T7}$.

Expression using the T7 RNA polymerase/$p_{T7}$; system relies upon (typically) a two-plasmid system: the first plasmid comprises the gene to be expressed and $p_{T7}$; the second plasmid comprises the gene for T7 RNA polymerase. The second plasmid, e.g. pGP1-2 (which comprises the gene for T7 RNA poylmerase; see Tabor and Richardson, *Proc.Natl.Acad. Sci. U.S.A.* 82: 1074–1078 (1985)), can either permanently reside in *E. coli* or can be introduced into *E. coli* with a specialized phage, such as, e.g., an M13 vector (such as, e.g., mGP1-2, see Tabor and Richardson), or a λ vector (such as, e.g., CE6, see Studier and Moffett, *J.Mol.Biol.,* 189: 113–130 (1986)) comprising the T7 RNA polymerase gene.

Typically, the second plasmid comprising the T7 RNA polymerase gene is under the control of a heat inducible *E. coli* promoter, i.e., by raising the temperature from, e.g., 30° C. to 42° C., the heat inducible *E. coli* promoter is switched on, which will in turn switch on the $P_{T7}$ promoter of the first plasmid, thereby leading to the expression of, e.g., the gene of interest. Thus, when using a T7 RNA polymerase/$p_{T7}$ expression system, the *E. coli* system comprises a heat-inducible promoter, such as, for example lambda $P_L$ With a $CI_{857}$ repressor.

Examples of vectors comprising $p_{T7}$ include, e.g., the pT7 series (pT715, pT7-6, and pT7-7, which are derivatives of pT7-14 1; see Tabor and Richardson, supra.) and the pET series (see Studier et al., *Methods EnZymol.* 185:60–89 (1990)).

Another vector system comprises a $p_L$ promoter gene. The $P_L$ promoter is derived from the λ bacteriophage and is one of the most powerful regulated *E. coli* promoter. Transcription from $P_L$ can be fully repressed and therefore plasmids comprising $p_L$ can be stabilized by the λ repressor, cI. This repressor is typically supplied by an *E. coli* host which comprises an integrated copy of a portion of the λ genome. Such an *E. coli* host, referred to as an "*E. coli* lysogen" is characterized as follows: (i) it supplies the λ regulatory proteins cI and N (an anti-termination function); and (ii) it does not provide lyric components that would normally lead to cell lysis. Accordingly, *E. coli* lysogens transfected with plasmids comprising, e.g., a gene of interest and $P_L$, can be grown initially to high density without expression of the gene and subsequently induced to synthesize the protein under inactivation of the repressor. Examples of $p_L$ based vectors are described in, e.g., U.S. Pat. No. 4,925,799 ("pAS1"), Shatzman and Rosenberg, "The pAS Vector System and Its Application to Heterologous Gene Expression in *Eschericia coli* ." *Heptalogy* 7:305–355 (1987), and Rosenberg et al., "The Use of pKC30 and its Derivatives for Controlled Expression of Genes." *Methods Enzymol* 101: 123–139 (1983).

The $p_{tac}$ promoter is a hybrid promoter based on the tac and lac promoters. de Boer, et al. "The tac promoter: A functional hybrid derived from the trp and lac promoters." *Proc.Natl.Acad. Sci.USA* 80:21–25 (1983); see also, Amann, et al. "Vectors bearing a hybrid trp-lac promoter useful for regulated expression of cloned genes in *Eschericia coli.*" Gene 25:167–178 (1983). Because $p_{tac}$ includes the lac operator region, it can be repressed by *E. coli* strains that overproduce the lac repressor, and be fully induced by addition of isopropyl β-D-thiogaloctoside (IPTG) thereto.

All of the foregoing references are incorporated herein by reference.

The choice of an appropriate vector/host system is within the realm of the particular needs of the artisan. A most preferred vector is based upon the $P_L$ promoter. Table I sets forth a representative (not exclusive) list of suitable vectors and hosts, as well as the sources thereof.

TABLE I

| Vector | Host* | Source |
|---|---|---|
| pBTac1 DNA | JM101, JM105, JM107, JM109 | (1) |
| pBTac2 DNA | JM101, JM105, JM107, JM109 | (1) |
| pNH8A | D121OPH, D1210 | (2) |
| pNH16A | D121OPH, D1210 | (2) |
| pNH18A | D121OPH, D1210 | (2) |
| pPROK-1 | JM109 | (3) |
| pEX2 | N4830-1 | (3) |
| PUC19 | JM101, JM105, JM107, JM109 | (4) |
| p33 | AR120, AR58 | (5) |
| pA33 | AR120, AR58 | (5) |
| $_pP_L$-Lamda | N99cI+-N4830-1 | (6) |

*E. COLI CELL
(1) = BOEHRINGER MANNHEIM
(2) = STRATAGENE CLONING SYSTEM
(3) = CLONETECH CLONING SYSTEMS
(4) = BETHESDA RESEARCH LABS
(5) = SMITHKLINE BECKMAN NOW SMITHKLINE BEECHAM
(6) = PHARMACIA LKB

For the following examples, the vectors pΔ33 and pBTac2 DNA were utilized in conjunction with the host strains AR120 and JM105, respectively, for the subcloning (initially from pUC19 vector) and expression of rSLO.3.

EXAMPLES

The following Examples directed to preferred embodiments are not intended, nor are they to be construed to be, limitations on the disclosure of the claims to follow.

Example 1

Preparation of Partially Digested Genomic Streptolysin O DNA

Genomic DNA was isolated from *Streptococcus pyogenes* (ATCC #10389) using the technique described in Kehoe, M. et al. *Infect. Immun.,* 55:3228–3232 (1987) (hereinafter "Kehoe, 1987"), which is incorporated herein by reference. Approximately 1 mg of *S. pyogenes* DNA was obtained using this procedure (925 μg).

To 370 μl of *S. pyogenes* DNA (2.5 μg/μl ) was added 300 μl of 10× High Salt Buffer (1.0M NaCl; 100 mM trishydroxyamino methane-chloride ("TRIS-Cl"), pH7.5; 100 mM $MgCl_2$; and 10 mM dithriothreotol ("DTT")), 2310 μl of deionized $H_2O$ and 20 μl of Bgl II (BRL, Gaithersburg, Md., Cat. #5213SA), for a final volume of 3000 μl. This mixture was maintained at 37° C. and incubated overnight.

To this incubated mixture was added 3000 μl of Reagent A (250 μl phenol, 250 μl chloroform, 10 μl isoamyl alcohol, 1 μl β-mercapthoethanol). This mixture was agitated prior to centrifugation in order to separate the aqueous and the organic layer. The aqueous supernantant was then precipitated with 0.3M NaOAc and 95% ethanol. The precipitate was then redissolved in 250 μl TE (10 mM TRIS-Cl, pH 7.5; 1 mM EDTA) and 25 μl of 10× loading dye (0.2M EDTA; 50% glycerol; 0.25% xylene cyanol; 0.25% bromophenol blue) was added thereto, followed by electrophoresis on 1% agarose gel. The Bgl II partially digested *S. pyogenes* genomic DNA fragments were then evaluated according to size.

As noted, SLO has an approximate molecular weight of 65,000 to 70,000 daltons. Each amino acid has an approximate molecular weight of 110 daltons, such that (conservatively estimating) a 70,000 dalton protein would be encoded by approximately 636 codons, or 1909 base pairs. Accordingly, the partially digested fragments of between about 2,000 to 2,500 base pairs (i.e., 2.0 to 2.5 Kb), as determined by the aforementioned gel electrophoresis method, were purified. The purified fragments were then resuspended in 150 μl of TE. For convenience, these are designated herein as "SLO inserts".

Example 2

Preparation of Streptolysin O Containing Plasmids

The vector utilized was pUC19 (BRL, Cat. #5364SA) cut with Bam HI (BRL, Cat. #5201SA).

To 1 μl of cut pUC19 vector was added 15 μl of the SLO inserts, 3 μl of 10X ligation buffer (660 mM TRIS-Cl, pH 7.5; 50 mM magnesium chloride; 10 mM DTT; 10 m MATP). A final volume of 30 μl was achieved by the addition of 8 μl of deionized $H_2O$. To this mixture was added 2 μl of T4 ligase (USB, 5 μg/μl); incubation thereof at room temperature proceeded overnight. For convenience, the resulting material is designated as "SLO plasmid candidates".

Example 3

Screening of SLO Plasmid Candidates

Host cells *E. coli* strain JM105 were transformed with the SLO plasmid candidates as follows. A vial containing 300 μl of frozen JM105 competent cell was thawed, and 16.0 μl of the SLO plasmid candidates was added thereto. This admixture was incubated on ice for 30 min, followed by heat shock in a 37° C. water bath for 2 min. Thereafter, the transfected JM105 solution was added to 2 ml of LB medium (10 g Bacto-tryptane; 5 g Bacto yeast extract; 10 g NaCl; 1 liter deionized water; pH 7.5 with sodium hydroxide), followed by shaking (200 RPM) for 30 min at 37° C. Plating was thereafter accomplished on LB Ampicillin plates, followed by incubation overnight at 37° C.; for convenience, these are designated "SLO transformants".

Screening was accomplished utilizing a unique procedure. Following overnight growth, the colonies were overlaid with 3 ml of 2.5% washed rabbit red blood cells in 0.8% agarose in PBS/10 m MDTT, which was spread to cover the plates. After 40 min of incubation at 37° C., colonies comprising SLO were surrounded by small zones of hemolysis. In order to confirm that these colonies comprised SLO, a 25-mer oligonucleotide probe derived from nucleotides 670 through 694, inclusive, of the reported DNA sequence of SLO (see *Kehoe,* 1987) was used as a probe. The probe was prepared with a BioSearch 8600 DNA synthesizer, and labelled with =p following the T4 polynucleotide kinase procedure described in Maniatis et al., *Molecular Cloning,* CSPL (1982), pp. 122–126 (hereinafter "*Molecular Cloning*").

The blood overlay screening technique proved to be an efficient and accurate method for rapidly screening the SLO expressed by the SLO transformants. Because a property of SLO is the ability thereof to lyse red blood cells, red blood cells from any source can be utilized, i.e., human, mouse, goat, rabbit, etc. Rabbit red blood cells are preferred due to the availability thereof.

An SLO clone that led to the expression of protein which evidenced hemolytic activity and which hybridized with the 25-mer probe was designated "pUC19-SLO-B". For convenience, the non-vector DNA sequence thereof is designated herein as "rSLO-candidates".

Example 4

Optimization of Expression and Determination of Solubility

In order to optimize the expression of rSLO-candidates, timed-digestion of rSLO-candidates using Bal31 was accomplished. Additionally, and as previously noted, solubility of the expressed protein ab initio, i.e., without further chemical modification once expressed, is of import. This is because non-soluble SLO is by definition inactive. Accordingly, an analysis was also made to determine if the expressed protein was soluble, i.e. was located in a supernatant as opposed to a pellet, following centrifugation.

The pUC19-SLO-B was initially cut with BstE II (New England Bio Labs, Cat. #162, 10 U/μl) as follows. To 20 μl of pUC19-SLO-B (2.5 μg/μl) was added 40 μl of 10× High Salt Buffer, 335 μl deionized $H_2O$, and 5 μl of BstE II. This admixture was incubated at 60° C. for 2 hrs, followed by extraction with 400 μl of Reagent A, and precipitation with 44 μl of 3M NaOAc (pH 4.8) in 888 μl of 95% ethanol. The precipitant was then redissolved in 40 μl $H_2O$. Thereafter, 90 μl of $H_2O$, 20 μl of 10× Bal-31 Buffer (120 mM $CaCl_2$; 120 mM $MgCl_2$, 2.0M NaCl; 0.2M TRIS-Cl, pH 8.0; 10 mM EDTA), and 50 μl of 1 mg/ml Bovine Serum Albumin, was admixed with the redissolved precipitant. This was followed by the addition of 10 μl of Bal-31 (New England Bio Labs, Cat. #213, 100 U/ml), for a total of 210 μl, followed by incubation at room temperature. To control the effects of Bal-31, 30 μl aliquots of the 210 μl total solution was removed at 30, 45, 60, 80, 105, 130 and 160 min post-Bal-31 addition, and these aliquots were each admixed in 3.3 μl of 0.2M EGTA, followed by storage on ice. After preparation and storage of the last aliquot, all seven aliquots were pooled, extracted with 230 μl of Reagent A, and precipitated with 23 μl of 3M NaOAc in 506 μl of 95% ethanol. The precipitate was then redissolved in 75 μl of $H_2O$.

A fill-in reaction followed by the addition of 5 μl of 2.5 mM dXTP, 10 μl of 10× Medium Salt Buffer (500 mM NaCl; 100 mM TRIS-Cl, pH 7.5; 100 mM $MgCl_2$; 10 mM DTT), and 10 μl of 100 mM of DTT to 75 μl of the redissolved precipitant, followed by the addition thereto of 6 μl of Klenow polymerase (5 U/μl), and incubation at room temperature for 4 hrs. This admixture was extracted with 100 μl of Reagent A, precipitation with 11 μl of 3M NaOAc in 22 μl of 100% ethanol, and resuspension of the precipitate in 40 μl of $H_2O$.

Following the fill-in reaction, 17 μl of the resuspended precipitate was admixed with 3 μl of a linker comprising a Bam HI sequence (New England Bio Labs, Cat #1021) and 5 μl of 5× linker ligation buffer (250 mM TRISCl, pH 7.6; 50 mM $MgC_2$; 5 mM DTT; 5 mM ATP; 2.5% (w/v) PEG 8000 (J. T. Baker, Cat. #U222-09)). This was followed by the addition thereto of 2 μl of T4 ligase (5 U/μl), and incubation thereof for 6 hrs at room temperature. For convenience, the resulting material is referred to as "ca/ew".

*E. coli* strain JM105 was transformed with ca/ew as described above, followed by overnight growth as described above in Example 3. To determine if the plasmids comprised the Bam HI linker, to 40 μl of ca/ew (0.5 μg/μl) was added 40 μl of 10× Medium Salt Buffer, and 320 μl deionized $H_2O$. To this mixture was added 5 μl EcoRI (BRL, Cat #5202 SA, 10 U/μl), followed by incubation at 37° C. for 2 hrs. In order to ensure that the plasmid was cut, gel electrophoresis (1% agarose gel) was conducted; this resulted in a smear of different sizes, indicating a successful cut. To the cut plasmid was added 8 μl of 5M NaCl, followed by 5 μl of Bam HI (10 U/μl. This mixture was incubated for 37° C. for 2 hrs. Determination of the size of the rSLO-candidate sequence subjected to Bal-31 digestion was conducted by gel electrophoresis (1% agarose gel). This resulted in a band of interest at about 1.2 to about 2.0 Kb which comprised rSLO-candidates. Thus, the initial fragments of 2.0 to 2.5 Kb which evidenced hemolytic activity had been significantly decreased in size.

The band which comprised rSLO-candidate was cut from the gel and purified in 15 μl of TE such that rSLO-candidate was available for ligation in pUC19 vector previously cut with Bam HI and ECoRI. In order to accomplish such ligation, 10 μl of the gel-purified rSLO-candidate was admixed with 4 μl of the previously prepared vector, 2 μl of 10× ligation buffer, 2 μl of 10 mM ATP, and 2 μl of deionized $H_2O$. To this admixture was then added 2 μl of T4 ligase, followed by incubation at room temperature for 6 hrs. *E. coli* host cell strain JM105 was transformed with these plasmids as above, and active colonies were screened by the red-blood cell overlay method disclosed above. Active colonies were then selected, inoculated in LB Medium/100 μg/ml Ampicillin and grown overnight under the conditions described above.

Following overnight growth, the cells were centrifuged for 5 min at 8000RPM at 4° C., and the resulting pellet resuspended in 2 ml of Reagent B (150 mM NaCl; 20 mM TRIS, pH 7.0; 1 mM EDTA). Thereafter, the resuspended cells were subjected to sonication for 2×30 sec. on ice, followed by centrifugation at 9500 RPM for 40 min at 4° C. using a Beckman JA20.1 centrifuge to obtain the expressed protein.

At this stage, if the rSLO-candidate led to the expression of a soluble protein, that protein would be located in the supernatant. Accordingly, analysis was conducted for the presence of rSLO-candidate in the supernatant using standard Western blot protocols for determination of an antigenically active protein. The results of such Western blot analysis indicated that there was an SLO fusion product in the supernatant which was recognized by horse anti-SLO antibodies. One such fusion product was selected and designated "rSLO.3 " For convenience, the DNA sequence leading to the expression of rSLO.3 is also referred to as rSLO.3. High level expression of rSLO.3 was thereafter attempted.

Example 5

High Level Expression of rSLO.3

Removal of rSLO.3 from the plasmid comprising pUC19 vector was effectuated as follows. To 15 μl of the plasmid comprising rSLO.3 (0.5 μg/μl ) was added to 40 μl of 10× Sma I Buffer (200 mM KCl; 100 mM TRIS-Cl, pH 8.0; 100 mM $MgCL_2$; 10 mM DTT), and 345 μl of deionized $H_2O$. To this mixture was added 5 μl Sma I (BRL, Cat #5228 SA, 10 U/μl), followed by incubation at 37° C. for 2 hrs . In order to ensure that the plasmid was cut, gel electrophoresis (1% agarose gel) was conducted; this resulted in a single band, indicating a successful cut. To the cut plasmid was added 8 μl of 5M NaCl, followed by 5 μl of Bam HI (10 U/μl). This mixture was incubated for 37° C. for 2 hrs . To ensure that the rSLO.3 sequence was successfully cut from the approximately 2.7 Kb pUC 19 vector, gel electrophoresis (1% agarose gel) was conducted. This resulted in two bands, one at about 2.7 Kb (the vector), and the other at about 1.4 Kb (rSLO.3). This band was cut from the gel and purified in 15 μl of deionized $H_2O$ such that rSLO.3 was available for ligation in pΔ33 vector previously cut with Bam HI and Sma I.

To 2 μl of above-derived rSLO.3 DNA was added 2 μl of the above described vector, 1.5 μl of 10× ligation buffer, 1.5 μl of 10 mM ATP, and 8 μl of deionized $H_2O$. To this admixture was added 2 μl of T4 ligase (10 U/μl), followed by incubation for 5 hrs at room temperature. Such incubation resulted in plasmids comprising rSLO.3 and pΔ33 vector.

*E. coli* strain AR120 was transformed with the above-described plasmids in accordance with the procedure outlined for *E. coli* strain JM105. Thereafter, a DNA mini prep described in *Current Protocols in Molecular Biology*, Ausubel, F. M. et al., Eds, John Wiley & Sons (New York) (1987), Section 1.6., followed by cutting the plasmids with Bam HI and Sal I (BRL, Cat. #5217 SA) to determine if the plasmids comprised rSLO.3. Those host cells transformed with plasmids comprising rSLO.3 were then subjected to induction via the nalidixic acid protocol. See Mort, J. E. et al "Maximizing gene expression from plasmid vectors containing the $\lambda P_L$ promoter: Strategies for overproducing transcription termination factor p." *PNAS USA,* 82: 88–92 (1985), which is incorporated herein by reference. As those in the art appreciate, nalidixic acid, which damages DNA, induces recA protein, a recovery protein for *E. coli* . A derivative benefit vis-a-vis overexpression is that recA has protease activity, which, inter alia, leads to inactivation of λcI+ repressor; this inactivation leads to overexpression by the $P_L$ promoter.

Specifically, colonies comprising the transformed AR120 were lifted from the agar plates and inoculated in Superboth (Base—12 g tryptone, 24 g yeast extract, 5 ml glycerol, 900 ml distilled $H_2O$; Salt (per liter of base-)—1.7 g $KH_2PO_4$, 15.8 g $K_2HPO_4$ (anhydrous) 100 ml distilled $H_2O$) plus 100 μg/ml ampicillin at 37° C. until the optical density of the medium at $A_{650}$ equaled 0.4. Thereafter, nalidixic acid was added to the inoculated mixture at a final concentration of 60 μg/ml and incubated at 37° C. for 4 hrs . Western blot analysis of the supernatant demonstrated the presence of rSLO.3

The DNA and amino acid sequences of rSLO.3 was thereafter determined (Lark Sequencing Technologies, Houston Tex.). A single stranded representation of the determined DNA sequence of rSLO.3 is presented in FIG. 1 and the determined amino acid sequence of rSLO.3 is presented in FIG. 2.

Example 6

Specific Activity of rSLO.3

Protein concentration and specific activity of non-purified SLO.3 was determined immediately following nalidixic acid induction.

Protein concentration for rSLO.3 crude extracts was derived using the BioRad Protein Assay method (Coomassie Blue G-250). Nalidixic acid induced protein mixtures were centrifuged at 8000 RPM for 5 min at 4° C. and the pellets resuspended in 500 μl sonication buffer (40 mM TRIS, pH 7.5; 1 mM EDTA; 1 mM DTT; 200 mM NaCl). The resuspended pellets were then sonicated for 2×30 sec on ice, followed by centrifugation at 12,000 RPM for 40 min at 4° C. Thereafter, 5 μl of the resuspended rSLO.3 mixture was analyzed for protein concentration (OD reading at $A_{595}$), and the protein concentration was determined to be 4.6 μg/μl.

Specific activity was determined by serial dilutions of the above described crude extract and addition thereto of washed rabbit red blood cells ("RRBC"), followed by spectrophotometric reading (OD reading at $A_{541}$). 5 ml of fresh rabbit blood was washed 2× with 45 ml of PBS including 10 mM DTT, followed by centrifugation at 2000 RPM for 5 min at 4° C. Thereafter, 1.125 ml of the washed rabbit red blood cells ("RRBC") were drawn from the bottom of the tube and 48.875 of PBS/10 mM DTT was added thereto. This resulted in a solution comprising 2.25% RRBC. For the hemolytic assays, 500 μl of the 2.25% RRBC was added to 500 μl of 1:2 serially diluted rSLO.3 in PBS/10 mM DTT, followed by incubation at 37° for 30 min.

These serial dilutions were spectrophotometrically analyzed (OD readings at $A_{541}$). This analysis indicated that 2 μl of the diluted rSLO.3 crude extract caused 50% hemolysis of the RRBC; 2 μl of the diluted extract is equivalent to 2 μl of the extract itself. Accordingly, the rSLO.3 crude extract evidenced one hemolytic unit ("HU") per two microliters, or 5000 HU/ml.

As noted, the protein concentration of the crude extract was determined to be 4.6 mg/ml. Accordingly, the specific activity of rSLO.3 derived from the pΔ33-AR120 expression system was 1087 HU/mg. It is noted that because these are values for a crude (i.e. non-purified) extract, these values are predicated upon total protein concentration of the extract. For a purified extract, the specific activity values increase.

Example 7

Recovery of rSLO.3

The following procedure is for approximately 200 grams of transformed host cells (i.e., approximately 6 grams total protein).

Transformed host cells were resuspended in 200 mls of Reagent C (40 mM TRIS, pH 7.5; 1 mM EDTA; 0.1% 2 -mercaptoethanol), followed by the addition of 100 mM PMSF. Thereafter, the cells were disrupted by sonication, followed by the addition of 4 ml of 100 mM PMSF. This admixture was centrifuged for 30 min at 4° C. at 15,000 RPM.

The resulting supernatant was removed and saved; 200 ml of Reagent C was added to the pellet, followed by the addition of 4 mls of 100 mM PMSF. The resuspended pellet was then sonicated, followed by centrifugation as above. The resulting supernatant was then removed and pooled with the previous supernatant, and the pH thereof was adjusted to 7.0 with NaOH.

To the final volume of supernatant was slowly added (with stirring at room temperature) Polymin P (Aldrich Chemicals) to a final concentration of 0.75%. This admixture was then centrifuged for 30 min at room temperature at 10,000 RPM, followed by retrieval of the supernatant. Solid sodium sulfate was slowly added with stirring to 80% saturation of the supernatant.

Thereafter, the admixture was stirred for 2 hrs at 4° C., followed by centrigation for 30 min at 4° C. at 15,000 RPM. The pellet was then retrieved and resuspended in 400 mls of saturated ammonium sulfate, pH 7.0. The admixture was then centrifuged for 30 min at 4° C. at 10,000 RPM, followed by retrieval of the pellet and resuspension thereof in 200 mls in Reagent D (20 mM TRIS, pH 7; 1 mM EDTA; 0.1% 2-mercaptoethanol).

The resuspended pellet was then dialyzed against 2 liters of Reagent D, with 4 changes, at 4° C. Sufficient room was left in the dialysis bag in that the volume of the sample increases. Following dialysis, the pH of the sample was checked, and adjusted to 7.0 with NaOH.

The sample was then loaded onto a Pharmacia Fast Flow S-Sepharose column equilibrated in Reagent D. A 400 ml bed volume was found to be sufficient to remove the mSLO.3/6 from the sample. The flow through, comprising *E. coli* proteins, was collected and discarded, and the column was washed with approximately 1 liter of Reagent D.

The rSLO.3 was eluted with 2×1 liter 0.0 to 0.4M NaCl gradient in Buffer B. The fractions were analyzed by SDS acrylamide gel (9%), and fractions with high amounts of rSLO.3 were pooled. Approximately 250 ml of pooled rSLO.3 was recovered.

Using the above procedure, approximately 60% of the original total protein (i.e. approximately 0.36 grams) was rSLO.3, which can be stored at 4° C. until needed.

Example 8

Purification of rSLO.3

Purification of rSLO.3 was accomplished to a purity of at least 80% using the following protocol.

Approximately 600 g of frozen cell paste derived in accordance with the protocol described in Example 9 was thawed (37° C.), resuspended in 3 liters of cold lysis buffer (40 mM TRIS-Cl, pH 7.0; 1 mm EDTA; 0.1% 2-mercaptoethanol; 2M Nacl; 4° C.) and sonicated for 60 min at 4°-10° C. with a Heat Systems Ultrasonics Continuous Flow sonicator (Farmingdale, N.Y., No. W-385). Thereafter, the material was centrifuged on a Beckman JA10 centrifuge at 9500 RPM for 40 min at 20° to 26° C.. Approximately 3 liters of supernatant was retrieved.

To the supernatant was added at 12.5% stock solution of Polymin P precipitant (Aldrich, Milwaukee, Wis.) to a final concentration of between 0.2 to 0.3%. The solution was then stirred for 1 hr at room temperature and the precipitate discarded. The pH of the liquid portion was then adjusted to 7.0 with NaOH. This liquid was then permitted to stand overnight at room temperature.

Thereafter, the solution was centrifuged as above, and a clear supernatant retrieved. The supernatant was then loaded onto a 1 liter phenyl-sepharose HIC column (Pharmacia, Piscataway, N.J.) at 2 ml/min. at room temperature. Thereafter, the column was washed with an elution buffer (20 mM TRIS-Cl, pH 7.0; 1 mM EDTA; 0.1% BME) at 7 ml/min. Fractions were monitored by SDS-PAGE electrophoresis using the Pharmacia Phast-Page™ System. Protein concentration was determined with the BioRad Protein Assay Kit. Fractions containing protein were then pooled.

The pooled fractions was then loaded onto a 1 liter Blue Affinity Column (BioRad, Richmond, Calif.) at 2 ml/mm at room temperature, followed by washing using the elution buffer described above at 2 ml/min. at room temperature for two column volumes.

Elution of bound protein was accomplished using an NaCL density gradient of 0.0 to 0.8M, pH 7.0. Fractions were monitored with the Phast-PAGE System and protein concentration determined with the BioRad Protein Assay Kit. A single peak was obtained at 0.3–0.4M on the NaCL density gradient.

Purity of the eluted rSLO.3 was evaluated using a Beckman DU 7500 spectrophotometer, based upon analysis of major band homogeneity obtained from gel electrophoresis (12% SDS-polyacrylamide) of six different amounts of the eluted rSLO.3 (16, 8, 4, 2, 1, 0.5 μg rSLO.3). The evaluated purity of rSLO.3 based upon major band homogeneity is set forth in Table 2:

TABLE 2

| rSLO.3 (μg) | Percent Homogeneity rSLO.3 |
|---|---|
| 0.5 | 99.0% |
| 1.0 | 99.0% |
| 2.0 | 94.4% |
| 4.0 | 82.4% |
| 8.0 | 81.4% |
| 16.0 | 80.1% |

For determination of hemolytic activity, the concentration of purified rSLO.3 was determined. A 1:25,600 titer of a 0.7 mg/ml concentration of purified rSLO.3 was required to obtain greater than 50% lysis of 2.5% RRBC. Accordingly, the specific hemolytic activity of purified rSLO.3 is about $3.6\times10^4$ HU/mg (25,600÷0.7).

As noted, the specific activity and percent hemolytic activity of specific versions of rSLO (purified rSLO.3), based upon the "specific activity" of wild-type SLO, is as follows:

TABLE 3

| | Wild-Type SLO | rSLO.3 |
|---|---|---|
| Specific Activity (Hemolytic Activity in Hemolytic Units/mg) | a) $1 \times 10^6$ b) $4 \times 10^5$ | $3.6 \times 10^4$ |
| Percent Hemolytic Activity of Wild-Type SLO | a) 100 b) 100 | 3.6 9 |

Example 9

In Vivo Toxicity Effects of rSLO.3

In order to evaluate in vivo toxicity effects of rSLO.3, Balb/c mice were administered undiluted and diluted intravenous injections of rSLO.3. Undiluted and diluted control suspension buffer was administered to an equivalent number of mice. To improve the intravenous injections, the mice were warmed under a heat lamp for 20–30 minutes of pre-injection. Approximately 20 mice were used for each condition.

For the undiluted rSLO.3, each mouse received an approximate dosage of 17 mg/kg, while for the diluted rSLO.3, each mouse received an approximate dosage of 1000 μg/kg. Control solution buffer did not affect the control mice.

Aside from minor ruffling for several minutes after injection, none of the mice receiving either diluted or undiluted rSLO.3 showed any ill effects from the intravenous administrations. Thus, while rSLO.3 is hemolytically active, mice receiving injections of rSLO.3 as described above did not expire.

Example 9

Subcloning of rSLO. 3

Having obtained, verified and sequenced rSLO.3, subcloning and expression thereof using another expression/vector system was initiated. The vector, pBTac 2 DNA (Boehringer Mannheim, Cat. No. 1081381, 10 μg) was cut with Hind III (BRL, Cat. No. 52075A, 10 U/ml) by admixing 30 μl of pBTac2 DNA (1 μg/μl), 30 μl of 10× Medium Salt Buffer, 240 μl deionized $H_2O$, followed by addition thereto of 5 μl of Hind III (BRL, Cat. #5207 SA, 10 U/μl). This admixture was incubated for 2 hrs at 37° C. Thereafter, the admixture was analyzed by agarose electrophoresis (1% agarose gel) to determine if the vector had been successfully cut; a single band indicated that the cut had been successful.

To the 305 μl admixture was added 300 μl of Reagent A. This admixture was then centrifuged for 5 min at 12,000 RPM on a Beckman microcentrifuge, followed by retrieval of the upper liquid layer. To this liquid layer was added 33 μl of 3M NaOAc (pH 4.8) and 660 μl of ethanol, followed by precipitation overnight at −20° C. This was followed by centrifugation for 10 min at 12,000 RPM on a Beckman microcentrifuge. The pellet was retrieved and dried by air. The dried pellet was then resuspended in 150 μl of deionized water.

In order to blunt (fill-in) one end of the Hind III cut vector, the 150 μl solution comprising the resuspended pellet was admixed with 10 μl of 20× dNTP (2.5 mM), 20 μl of 10× MSB and 20 μl of 100 mM DTT. This was followed by the addition of 4 μl of Klenow polymerase (New England Biolabs, Cat. No. 210, 5 U/ml) and incubation at room temperature for 7 hrs. Thereafter, 300 μl of Reagent A was added to the incubated mixture, followed by centrifugation for 5 min at 12,000 RPM. The upper liquid layer was retrieved and precipitated as above. The dried pellet was then resuspended in 30 μl of deionized $H_2O$. For convenience, the filled-in, Hind III cut vector is referred to as "vec.rb".

Thereafter, vec.rb was cut with Bam HI (BRL, Cat No. 5201 SA, 10 U/μl). To 30 μl of vec.rb was added 30 μl of 10× High Salt Buffer and 240 μl of deionized $H_2O$. To this admixture was added 5 μl of Bam HI, followed by incubation for 2 hrs at 37° C. To the incubated mixture was added 300 μl of Reagent A, followed by centrifugation as above. The upper liquid layer was retrieved and precipitated as above. The dried pellet was then resuspended in 20 μl of deionized $H_2O$. The resuspended pellet comprised Hind III cut, filled-in, Bam HI cut pBTac2 DNA.

The rSLO.3 was removed from the plasmid described above as follows. To 40 μl of the plasmid comprising rSLO.3 (1 μg/1 μl) was added 10× SmaI Buffer, and 320 μl deionized $H_2O$. To this mixture was added 5 μl Sma I (10 U/μl), followed by incubation at 37° C. for 2 hrs. In order to ensure that the plasmid was cut, gel electrophoresis (1% agarose gel) was conducted; this resulted in a single band, indicating a successful cut. To the cut plasmid was added 8 μl of 5M NaCl, followed by 5 μl of Bam HI (10 U/μl). This mixture was incubated for 37° C. for 2 hrs . To ensure that the rSLO.3 sequence was successfully cut from the approximately 6.3 Kb pΔ33 vector, gel electrophoresis (1% agarose gel) was conducted. This resulted in two bands, one at about 6.3 Kb (the vector), and the other at about 1.4kB (rSLO.3). The 1.4 Kb band was cut from the gel and purified in 20 μl of deionized $H_2O$ such that mSLO.3/6 was available for ligation in the prepared pBTac2 vector.

To 3 μl of the vector was added 2 μl of mSLO.3/6, 1.5 μl of 10× Ligation Buffer (0.66M TRIS-Cl (pH 7.5), 50 mM $MgCl_2$, 50 mM DTT, 10 mM ATP), 1.5 μl of 10 mM ATP and 7 μl of deionized $H_2O$. Thereafter, 1.5 μl of T4 Ligase was added thereto, followed by incubation overnight at room temperature. For convenience, this mixture is referred to as the "subclone$_r$".

*E. coli* strain JM105 was transfected with subclone$_r$ as follows. A vial containing 300 μl of frozen JM105 competent cell was thawed, and 8.0 μl of subclone$_r$ was added thereto. This admixture was incubated on ice for 30 min, followed by heat shock in a 37° C. water bath for 2 min. Thereafter, the transformed JM105 solution was added to 2 ml of LB medium (10 g Bacto-tryptane; 5 g Bacto yeast extract; 10 g NaCl; 1 l deionized water; pH 7.5 with sodium hydroxide), followed by shaking (200 RPM) for 30 min at 37° C. Plating was thereafter accomplished on LB Ampicillin plates, followed by growth overnight at 37° C. Screening was accomplished using the blood overlay method disclosed above, and colonies evidencing hemolysis were selected.

Selected screened colonies comprising rSLO.3 subclones were innoculted in 12 ml of Superbrothampicillin broth. Induction was accomplished by the addition of isoprpyl-β-D-thiogalactopyranoside ("IPTG"), at a final concentration of 1 mM , to the culture broth when the culture broth had an $OD_{600}$ reading of 0.7. 12 ml of the resulting solution was centrifuged at 8000 RPM for 10 min at 4° C. and the resulting pellet resuspended in 1.2 ml of PBS/10 mM DTT. The resuspended pellet was sonicated for 1.5 min; the protein concetration of the sonicated extract was determined using the BioRad Protein Assay protocol described above. The protein concentration was determined to be 9.3 mg/ml. This data was used to determine the specific hemolytic activity of the sonicated extract by titer based upon the 50% lyses of 2.5% washed rabbit red blood cell protocol described above. The hemolytic activity based upon titer of the culture comprising rSLO.3 was determined to be $2.69\times10^4$ HU/mg.

The foregoing Examples are directed to the generation of an SLO genomic library. As those in the art appreciate, another type of library which is much less complex than a genomic DNA library is a "complementary DNA", or "cDNA", library cDNA is derived directly from mRNA; therefore, by definition, the cDNA library is comprised of regions of translation. Methods for deriving cDNA libraries based upon mRNA complementary to mSLO DNA are considered to be within the purview of the skilled artisan such that cDNA-based libraries for mSLO are a part of this disclosure.

PROTEIN FOLDING

As the linear arrangement of nucleotides defines a specific codon, the arrangement, or sequence, of amino acids defines the protein, including the particular function thereof. However, while the particular amino acid sequence is important with respect to the identity of the protein, the particular three dimensional shape that the protein exhibits is of similar import. Such specificity in terms of shape, in essence, co-defines the properties of the protein because the shape of the protein enables the protein to specifically interact with other molecules that will only recognize that particular protein shape.

Most proteins spontaneously fold into their correct shape. By treating the protein with certain denaturing solvents, the protein can "unfold" into a flexible chain. When the denaturing agent is removed, portions of the flexible chain may refold into their original conformation. This is because one of the most important factors governing the folding of a protein is the distribution of polar (hydrophillic, or "water-hating") and non-polar (hydrophobic, or "water-loving") side chains of the amino acids of that protein. Denaturing solvents interfere with the polarity of the amino acid side chains. The following amino acids have polar side chains: Asn; Gln; Ser; Thr; and Tyr. The following amino acids have non-polar side chains: Gly; Ala; Val; Leu; Iso; Pro; Phe; Met; Trp; and Cys. Amino acids with basic and acidic side chains are very polar. The following amino acids have basis side chains: Lys; Arg; and His. The following amino acids have acidic side chains: Asp and Glu.

The environment in which proteins naturally exist is, by definition, a non-denaturing environment, which is most typically aqueous. Accordingly, the hydrophobic side chains of a protein tend to be pushed together in the interior of the protein molecule, which enables these to avoid contact with the aqueous environment. Polar side chains, on the other hand, tend to arrange themselves near the outside of the protein molecule, where they can interact with water and other polar molecules.

While the molecular mechanisms by which a linear DNA sequence is transcribed and translated into a precise amino acid sequence of the corresponding polypeptide is well understood, exactly how the polypeptide chain folds simultaneously and autonomously into its three-dimensional structure is not clearly understood. However, the real potential of synthetic DNA, i.e. DNA synthesized via recombinant techniques, will be realized in the area of protein design. In order for this to be realized, however, the mechanism of protein folding well have to be more succinctly clarified. While the general problem of predicting protein structure from the sequence is elusive (principally because no rules have emerged that allow structure to be related to sequence), it is clear that certain portions of the sequence are important to the structure and other portions are relatively unimportant from a structural point of view such that substitutions or modifications can be made at these portions. Accordingly, it is assumed that portions of the sequence of a protein contribute significantly to the stability of the folded protein structure.

While predicting a protein structure from the protein sequence is elusive, proteins, by definition, have unique three-dimensional structures which can be determined. The following methodologies, for example, can be used in the determination of protein structure: Crystallography; Optical Activity, Nuclear Magnetic Resonance Spectroscopy.

a) Crystollagraphy

Proteins are capable of forming crystals. Proteins usually crystallize in a condition of saturation or supersaturation which can be achieved by altering one or more of a number of variables that affect the solubility of the proteins. Thus, by altering the ionic strength of the solution or by utilization of organic polymers, e.g., polyethylene glycol, proteins can be crystallized. Techniques for growing protein crystals are set forth in Narang, S. A. *Protein Engineering: Approaches to the Manipulation of Protein Folding* (Butterworth, Publisher, Stoneham, Mass., 1990), Chpt. 6 (hereinafter "Narang"). The preceding text book is incorporated herein by reference in its entirety. Having crystallized the protein, the techniques of x-ray, neutron, and electron diffraction can be used to determine to structure of the protein, with x-ray diffraction being preferred. The protein structure in the crystal is assumed to be at or near the minimum conformational free energy of the molecule for the crystal form.

b) Optical Activity

The optical activity of polypeptides/proteins due to the asymmetric centers of the amino acids and to the asymmetric conformations thereof, can be utilized to determine the structure of polypeptides/proteins. This asymmetry causes proteins to interact differently with right- and left-circularly polarized light; if the two beams consequently travel at different speeds through the protein, polarized light is rotated. Optical rotatory dispersion ("ORD") is the dependence of this rotation upon wavelength. In a wavelength region where the protein molecule does not absorb light, the rotation varies gradually with wavelength, but in an absorbance region, the rotation first increases sharply in one direction, falls to zero at the absorption maximum, and then ristes sharply in the opposite direction. There will also be unequal absorptoin of left- and right-circularly polarized light; this is referred to as circular dichroism ("CD"). Both CD and OES spectra of a protein are very sensitive to the structural conformation thereof. Folded proteins generally have significant optical activity in the near-UV region (250–300 nm).

c) Nuclear Magnetic Resonnance Spectroscopy

Nuclear Magnetic Resonnance Spectroscopy, using, e.g., $^{1}H$, $^{13}C$, $^{15}N$, $^{13}P$ or $^{2}H$, has proven to be of great use in studying protein structure in solution. Focusing on 1H, each hydrogen atom in a molecule has a nuclear magnetic spin, i.e. the nuclei of the atom act like tiny magnets. In the absence of an external magnetic field, the magnetic moments of the protons are randomly oriented. In a Nuclear Magnetic Resonnance experiment, a strong external magnetic field is applied to the sample along a specified direction, resulting in a net alignment of the magnetic moments and a net macroscopic magnetization along the specified directional axis; a short radio-frequency pulse of appropriate strength is then applied, knocking the magnetization vector away from this axis. As the magnetization recovers, a transient radio-frequency signal is recorded as a function of time. A fourier-transform of this signal then yields a frequency spectrum. Each proton in the molecule gives rise to a peak in this spectrum occurring at some characteristic resonnance frequency determined by the local electronic environment of that proton. The resonnance frequency of a particular proton is called its "chemical shift" and is measured as an offset from some reference frequency. Structured information from NMR is derived from the nuclear Overhauser effect ("NOE", which determines whether a pair of protons are near each other in space) and the coupling constants of protons that are separated by three or fewer chemical bonds. NOE and coupling constants provide one-dimensional data; two-dimensional data is provided by inter alia nuclear Overhauser enhancement spectroscopy (NOESY) and two-dimensional correlation spectroscopy (COSY); and from such data, three-dimensional protein structures can be determined.

In view of the foregoing information set forth with respect to determination of the three-dimensional structure of protein molecules, the following claims directed to DNA macromolecules and amino acids inherently include the three dimensional structures associated with the protein molecules expressed thereby.

The Examples herein are not to be construed as limited to specific vectors, plasmids and host cells which are preferred. The rSLO described herein is not to be construed as limited solely to the preferred rSLO designated rSLO.3, or to the preferred vectors, plasmids and host cells. Similarly, the preferred rSLO.3 in no way constitute an admission, either actual or implied, that the DNA and amino acid sequences thereof are the only DNA and amino acid sequences to which Applicants are entitled. They are entitled to the full breadth of protection under applicable patent laws.

For purposes of claiming materials by designation, AR120 transformed with plasmids comprising pΔ33-rSLO.3 and JM105 transformed with plasmids comprising pBTac2 DNA-rSLO.3 were deposited on Aug. 23, 1991 with the American Type Culture Collection (ATCC), 12301 Parklawn Drive, Rockville, Md., 20852, under the provisions of the Budapest Treaty for the International Recognition of the Deposit of Microorganisms for the Purpose of Patent Procedure. These were tested by the ATCC on Aug. 27, 1991, and determined to both be viable. The ATCC has assigned the deposit numbers ATCC 68675 and ATCC 68677, respectively, to these materials.

Based upon the disclosure herein, those skilled in the art can readily obtain fragments of the DNA sequence set forth in FIG. 1 such that the fragment continues to maintain at least one epitopic site characteristic of wild-type SLO and maintains hemolytic characteristics. Furthermore, and as noted, conservative substitutions of nucleotides can be made without concomitant changes in the amino acid sequence, as those in the art understand and appreciate. For example, "computerized back translation" techniques can be used, whereby the amino acid sequence is analyzed by a computer and the computer determines the optimum nucleotides to utilize in the codons necessary to encode such amino acids. Additionally, as the DNA synthesis art progresses such that oligonucleotides having the length of the DNA sequence of FIG. 1 can be rapidly obtained, one can synthesize that sequence as appropriate with such advances in the art.

Because the screening of SLO derivatives can be readily accomplished using the above-described blood overlay technique, numerous SLO derivative candidates can be rapidly evaluated. Accordingly, those skilled in the art can readily use this technique to derive SLO derivative analog candidates, rapidly screen these candidates for indications of hemolytic activity, and determine the nucleic acid and amino acid sequences of analogs.

Accordingly, while the Examples herein are directed to a specific SLO variant, rSLO.3, and because having had this advance in the art placed in their possession, those in the art can utilize techniques known to the art to adapt this advance to their own ends, Applicant's invention is seen to comprehend SLO derivatives having the characteristics as defined, and is not limited to the specific derivative disclosed in the Examples.

Although the present invention has been described in considerable detail with regard to certain preferred embodiments thereof, other embodiments within the scope of the teachings of the present invention are possible. As such, while the production of a specific SLO derivative has been described in detail, this is to be construed as an exemplar. Accordingly, neither the disclosure, nor the claims to follow, are intended, nor should be construed to be, limited by the descriptions of the preferred embodiments contained herein.

What is claimed is:

1. A purified and isolated DNA sequence encoding a hemolytically active, soluble derivative of Streptolysin O, wherein said DNA sequence is as set forth in FIG. 1 (SEQ. ID NO: 1).

2. A prokaryotic or eukaryotic host cell transformed or transfected with a DNA sequence according to claim 1 in a manner allowing the host cell to express a hemolytically active, soluble derivative of Streptolysin O.

3. A DNA plasmid comprising a DNA vector and a DNA sequence according to claim 1.

4. A hemolytically active and soluble derivative of Streptolysin O having the amino acid sequence set forth in FIG. 2 (SEQ. ID No: 2).

5. A transformed or transfected mammalian host cell according to claim 2.

6. The DNA plasmid of claim 3, wherein the DNA vector comprises a high copy plasmid.

* * * * *

UNITED STATES PATENT AND TRADEMARK OFFICE

CERTIFICATE OF CORRECTION

PATENT NO. : 5,378,620
DATED : August 30, 1991
INVENTOR(S) : Craig W. Adams

It is certified that error appears in the above-identified patent and that said Letters Patent is hereby corrected as shown below:

Column 13,
Line 43, change "2μl" to -- 0.2 μl --
Line 45, change "two microliters" to -- 0.2 μl --

Signed and Sealed this

Eleventh Day of December, 2001

Attest:

NICHOLAS P. GODICI

*Attesting Officer*

*Acting Director of the United States Patent and Trademark Office*

UNITED STATES PATENT AND TRADEMARK OFFICE

CERTIFICATE OF CORRECTION

PATENT NO. : 5,378,620

DATED : January 3, 1995

INVENTOR(S) : Craig W. Adams and Eva Y. Wang

It is certified that error appears in the above-identified patent and that said Letters Patent is hereby corrected as shown below:

Column 17,

Lines 12 and 14, change “mSLO.3/6” to -- rSLO.3 --

Signed and Sealed this

Tenth Day of June, 2003

JAMES E. ROGAN

*Director of the United States Patent and Trademark Office*

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 1524 base pairs
( B ) TYPE: Nucleic acid
( C ) STRANDEDNESS: double
( D ) TOPOLOGY: linear ( i i ) MOLECULE TYPE: genomic DNA ( v i ) ORIGINAL SOURCE:
( A ) ORGANISM: Streptococcus pyogenes ( v i i ) IMMEDIATE SOURCE:
( A ) LIBRARY: genomic
( B ) CLONE: rSLO.3

( x i ) SEQUENCE DESCRIPTION: SEQ ID NO:: 1:

ATG GAT CCG TCA GAA GAC AAA AAA AAG AGC GAA GAA GAT CAC ACT GAA 48

GAA ATC AAT GAC AAG ATT TAT TCA CTA AAT TAT AAT GAG CTT GAA GTA 96

CTT GCT AAA AAT GGT GAA ACC ATT GAA AAT TTT GTT CCT AAA GAA GGC 144

GTT AAG AAA GCT GAT AAA TTT ATT GTC ATT GAA AGA AAG AAA AAA AAT 192

ATC AAC ACT ACA CCA GTC GAT ATT TCC ATC ATT GAC TCT GTC ACT GAT 240

AGG ACC TAT CCA GCA GCC CTT CAG CTG GCT AAT AAA GGT TTT ACC GAA 288

AAC AAA CCA GAC GCG GTA GTC ACC AAG CGA AAC CCA CAA AAA ATC CAT 336

ATT GAT TTA CCA GGT ATG GGA GAC AAA GCA ACG GTT GAG GTC AAT GAC 384

CCT ACC TAT GCC AAT GTT TCA ACA GCT ATT GAT AAT CTT GTT AAC CAA 432

TGG CAT GAT AAT TAT TCT GGT GGT AAT ACG CTT CCT GCC AGA ACA CAA 480

TAT ACT GAA TCA ATG GTA TAT TCT AAG TCA CAG ATT GAA GCA GCT CTA 528

AAT GTT AAT AGC AAA ATC TTA GAT GGT ACT TTA GGC ATT GAT TTC AAG 576

TCG ATT TCA AAA GGT GAA AAG AAG GTG ATG ATT GCA GCA TAC AAG CAA 624

ATT TTT TAC ACC GTA TCA GCA AAC CTT CCT AAT AAT CCT GCG GAT GTG 672

TTT GAT AAA TCA GTG ACC TTT AAA GAG TTG CAA CGA AAA GGT GTC AGC 720

AAT GAA GCT CCG CCA CTC TTT GTG AGT AAC GTA GCC TAT GGT CGA ACT 768

GTT TTT GTC AAA CTA GAA ACA AGT TCT AAA AGT AAT GAT GTT GAA GCG 816

GCC TTT AGT GCA GCT CTA AAA GGA ACA GAT GTT AAA ACT AAT GGA AAA 864

TAC TCT GAT ATC TTA GAA AAT AGC TCA TTT ACA GCT GTC GTT TTA GGA 912

GGA GAT GCT GCA GAG CAC AAT AAG GTA GTC ACA AAA GAC TTT GAT GTT 960

ATT AGA AAC GTT ATC AAA GAC AAT GCT ACC TTC AGT AGA AAA AAC CCA 1008

GCT TAT CCT ATT TCA TAC ACC AGT GTT TTC CTT AAA AAT AAT AAA ATT 1056

GCG GGT GTC AAT AAC AGA ACT GAA TAC GTT GAA ACA ACA TCT ACC GAG 1104

-continued

| | | | | | | | | | | | | | | | | |
|---|---|---|---|---|---|---|---|---|---|---|---|---|---|---|---|---|
| TAC | ACT | AGT | GGA | AAA | ATT | AAC | CTG | TCT | CAT | CAA | GGC | GCG | TAT | GTT | GCT | 1152 |
| CAA | TAT | GAA | ATC | CTT | TGG | GAT | GAA | ATC | AAT | TAT | GAT | GAC | AAA | GGA | AAA | 1200 |
| GAA | GTG | ATT | ACA | AAA | CGA | CGT | TGG | GAT | AAC | AAC | TGG | TAT | AGT | AAG | ACA | 1248 |
| TCA | CCA | TTT | AGC | ACA | GTT | ATC | CCA | CTA | GGA | GCT | AAT | TCA | CGA | AAT | ATA | 1296 |
| CGT | ATC | ATG | GCT | AGA | GAG | TGC | ACC | GGC | TTA | GCT | TGG | GAA | TGG | TGG | CGA | 1344 |
| AAA | GTG | ATC | GAC | GAA | AGA | GAT | GTG | AAA | CTG | TCT | AAA | GAA | ATC | AAT | GTC | 1392 |
| AAC | ATC | TCA | GGA | TCA | ACC | CTG | AGC | CCA | TAT | GGT | TCG | ATT | ACT | TAT | AAG | 1440 |
| TAG | GAC | TGG | TTC | AAG | AGG | TTC | GTC | AAG | CAC | CTT | GAT | GCT | GCT | TAT | CTC | 1488 |
| TTG | AGA | TCC | CCG | GGT | AGG | CCT | AGT | TAA | CTA | GTC | GAC | | | | | 1524 |

( 2 ) INFORMATION FOR SEQ ID NO: 2:

( i ) SEQUENCE CHARACTERISTICS:

( A ) LENGTH: 480 amino acids ( B ) TYPE: Amino Acid ( C ) TOPOLOGY: linear ( i i ) MOLECULE TYPE: protein ( i x ) FEATURE:
( A ) NAME/KEY: Signal sequence
( B ) LOCATION: amino acid 98 to amino acid 571 of SLO
( C ) IDENTIFICATION METHOD: experimentally determined based upon production of soluble, hemolytically active SLO from recombinant vector
( D ) OTHER INFORMATION: Lyses red blood cells ( x i ) SEQUENCE DESCRIPTION: SEQ ID NO:: 2:

| | | | | | | | | | | | | | | | |
|---|---|---|---|---|---|---|---|---|---|---|---|---|---|---|---|
| Met | Asp | Pro | Ser | Glu | Asp | Lys | Lys | Lys | Ser | Glu | Glu | Asp | His | Thr | Glu |
| -2 | -1 | | | | | 5 | | | | | 10 | | | | |
| Glu | Ile | Asn | Asp | Lys | Ile | Tyr | Ser | Leu | Asn | Tyr | Asn | Glu | Leu | Glu | Val |
| 15 | | | | | 20 | | | | | 25 | | | | | 30 |
| Leu | Ala | Lys | Asn | Gly | Glu | Thr | Ile | Glu | Asn | Phe | Val | Pro | Lys | Glu | Gly |
| | | | | 35 | | | | | 40 | | | | | 45 | |
| Val | Lys | Lys | Ala | Asp | Lys | Phe | Ile | Val | Ile | Glu | Arg | Lys | Lys | Lys | Asn |
| | | | 50 | | | | | 55 | | | | | 60 | | |
| Ile | Asn | Thr | Thr | Pro | Val | Asp | Ile | Ser | Ile | Ile | Asp | Ser | Val | Thr | Asp |
| | | 65 | | | | | 70 | | | | | 75 | | | |
| Arg | Thr | Tyr | Pro | Ala | Ala | Leu | Gln | Leu | Ala | Asn | Lys | Gly | Phe | Thr | Glu |
| | 80 | | | | | 85 | | | | | 90 | | | | |
| Asn | Lys | Pro | Asp | Ala | Val | Val | Thr | Lys | Arg | Asn | Pro | Gln | Lys | Ile | His |
| 95 | | | | | 100 | | | | | 105 | | | | | 110 |
| Ile | Asp | Leu | Pro | Gly | Met | Gly | Asp | Lys | Ala | Thr | Val | Glu | Val | Asn | Asp |
| | | | | 115 | | | | | 120 | | | | | 125 | |
| Pro | Thr | Tyr | Ala | Asn | Val | Ser | Thr | Ala | Ile | Asp | Asn | Leu | Val | Asn | Gln |
| | | | 130 | | | | | 135 | | | | | 140 | | |
| Trp | His | Asp | Asn | Tyr | Ser | Gly | Gly | Asn | Thr | Leu | Pro | Ala | Arg | Thr | Gln |
| | | 145 | | | | | 150 | | | | | 155 | | | |
| Tyr | Thr | Glu | Ser | Met | Val | Tyr | Ser | Lys | Ser | Gln | Ile | Glu | Ala | Ala | Leu |
| | 160 | | | | | 165 | | | | | 170 | | | | |
| Asn | Val | Asn | Ser | Lys | Ile | Leu | Asp | Gly | Thr | Leu | Gly | Ile | Asp | Phe | Lys |
| 175 | | | | | 180 | | | | | 185 | | | | | 190 |
| Ser | Ile | Ser | Lys | Gly | Glu | Lys | Lys | Val | Met | Ile | Ala | Ala | Tyr | Lys | Gln |
| | | | | 195 | | | | | 200 | | | | | 205 | |
| Ile | Phe | Tyr | Thr | Val | Ser | Ala | Asn | Leu | Pro | Asn | Asn | Pro | Ala | Asp | Val |

-continued

| | | | | | | | | | | | | | | | |
|---|---|---|---|---|---|---|---|---|---|---|---|---|---|---|---|
| | | | 210 | | | | | 215 | | | | | 220 | | |
| Phe | Asp | Lys | Ser | Val | Thr | Phe | Lys | Glu | Leu | Gln | Arg | Lys | Gly | Val | Ser |
| | | 225 | | | | | 230 | | | | | 235 | | | |
| Asn | Glu | Ala | Pro | Pro | Leu | Phe | Val | Ser | Asn | Val | Ala | Tyr | Gly | Arg | Thr |
| | 240 | | | | | 245 | | | | | 250 | | | | |
| Val | Phe | Val | Lys | Leu | Glu | Thr | Ser | Ser | Lys | Ser | Asn | Asp | Val | Glu | Ala |
| 255 | | | | | 260 | | | | | 265 | | | | | 270 |
| Ala | Phe | Ser | Ala | Ala | Leu | Lys | Gly | Thr | Asp | Val | Lys | Thr | Asn | Gly | Lys |
| | | | | 275 | | | | | 280 | | | | | 285 | |
| Tyr | Ser | Asp | Ile | Leu | Glu | Asn | Ser | Ser | Phe | Thr | Ala | Val | Val | Leu | Gly |
| | | | 290 | | | | | 295 | | | | | 300 | | |
| Gly | Asp | Ala | Ala | Glu | His | Asn | Lys | Val | Val | Thr | Lys | Asp | Phe | Asp | Val |
| | | 305 | | | | | 310 | | | | | 315 | | | |
| Ile | Arg | Asn | Val | Ile | Lys | Asp | Asn | Ala | Thr | Phe | Ser | Arg | Lys | Asn | Pro |
| | 320 | | | | | 325 | | | | | 330 | | | | |
| Ala | Tyr | Pro | Ile | Ser | Tyr | Thr | Ser | Val | Phe | Leu | Lys | Asn | Asn | Lys | Ile |
| 335 | | | | | 340 | | | | | 345 | | | | | 350 |
| Ala | Gly | Val | Asn | Asn | Arg | Thr | Glu | Tyr | Val | Glu | Thr | Thr | Ser | Thr | Glu |
| | | | | 355 | | | | | 360 | | | | | 365 | |
| Tyr | Thr | Ser | Gly | Lys | Ile | Asn | Leu | Ser | His | Gln | Gly | Ala | Tyr | Val | Ala |
| | | | 370 | | | | | 375 | | | | | 380 | | |
| Gln | Tyr | Glu | Ile | Leu | Trp | Asp | Glu | Ile | Asn | Tyr | Asp | Asp | Lys | Gly | Lys |
| | | 385 | | | | | 390 | | | | | 395 | | | |
| Glu | Val | Ile | Thr | Lys | Arg | Arg | Trp | Asp | Asn | Asn | Trp | Tyr | Ser | Lys | Thr |
| | 400 | | | | | 405 | | | | | 410 | | | | |
| Ser | Pro | Phe | Ser | Thr | Val | Ile | Pro | Leu | Gly | Ala | Asn | Ser | Arg | Asn | Ile |
| 415 | | | | | 420 | | | | | 425 | | | | | 430 |
| Arg | Ile | Met | Ala | Arg | Glu | Cys | Thr | Gly | Leu | Ala | Trp | Glu | Trp | Trp | Arg |
| | | | | 435 | | | | | 440 | | | | | 445 | |
| Lys | Val | Ile | Asp | Glu | Arg | Asp | Val | Lys | Leu | Ser | Lys | Glu | Ile | Asn | Val |
| | | | 450 | | | | | 455 | | | | | 460 | | |
| Asn | Ile | Ser | Gly | Ser | Thr | Leu | Ser | Pro | Tyr | Gly | Ser | Ile | Thr | Tyr | Lys |
| | | 465 | | | | | 470 | | | | | 475 | | | |